(12) United States Patent
Giese et al.

(10) Patent No.: US 11,224,529 B2
(45) Date of Patent: Jan. 18, 2022

(54) TUBULAR KNITTED STENTS

(71) Applicant: Eucatech AG, Weil am Rhein (DE)

(72) Inventors: Michael Giese, Rheinfelden (DE); Timo Schneiderhan, Bad Krozingen (DE)

(73) Assignee: EUCATECH AG, Weil am Rhein (DE)

( * ) Notice: Subject to any disclaimer, the term of this patent is extended or adjusted under 35 U.S.C. 154(b) by 398 days.

(21) Appl. No.: 16/415,032

(22) Filed: May 17, 2019

(65) Prior Publication Data

US 2019/0350730 A1  Nov. 21, 2019

(30) Foreign Application Priority Data

May 18, 2018 (EP) .................................. 18173369

(51) Int. Cl.
| | | |
|---|---|---|
| *A61F 2/90* | (2013.01) | |
| *A61F 2/07* | (2013.01) | |
| *D04B 1/22* | (2006.01) | |
| *D04B 9/44* | (2006.01) | |
| *D04B 15/10* | (2006.01) | |

(52) U.S. Cl.
CPC .................. *A61F 2/90* (2013.01); *A61F 2/07* (2013.01); *D04B 1/225* (2013.01); *D04B 9/44* (2013.01); *D04B 15/10* (2013.01); *A61F 2210/0014* (2013.01); *A61F 2240/001* (2013.01); *A61F 2250/0098* (2013.01); *D10B 2101/20* (2013.01); *D10B 2509/06* (2013.01)

(58) Field of Classification Search
CPC ................. A61F 2/90; A61F 2/06; A61F 2/07
See application file for complete search history.

(56) References Cited

U.S. PATENT DOCUMENTS

| | | |
|---|---|---|
| 2,752,952 A | 7/1956 | Dauphinais |
| 5,913,896 A | 6/1999 | Boyle et al. |
| 6,221,099 B1 | 4/2001 | Andersen et al. |
| 2007/0073374 A1 | 3/2007 | Anderl et al. |
| 2013/0211496 A1 | 8/2013 | Buck |

FOREIGN PATENT DOCUMENTS

| | | |
|---|---|---|
| DE | 623504 C | 12/1935 |
| DE | 10301600 A1 | 7/2004 |
| WO | 2015114869 A1 | 8/2015 |

OTHER PUBLICATIONS

Spencer, "Elements of Knitted Loop Structure", Knitting Technology: A Comprehensive and Practical Guide, Third Edition, Chapter 5, Woodhead Publishing Limited, Apr. 27, 2001.
Extended European Search Report from EP Application No. 18173369.2, dated Nov. 27, 2018.

*Primary Examiner* — Jason-Dennis N Stewart

(74) *Attorney, Agent, or Firm* — Workman Nydegger

(57) ABSTRACT

A tubular knitted stent or stent graft for placement in a lumen or body passage is compressible, thus presenting a compressed outer diameter and a non-compressed outer diameter. The stent or stent graft has knitted loops each having a loop width, wherein the loop width to non-compressed outer diameter ratio is larger than 0.2 for at least one knitted loop.

13 Claims, 7 Drawing Sheets

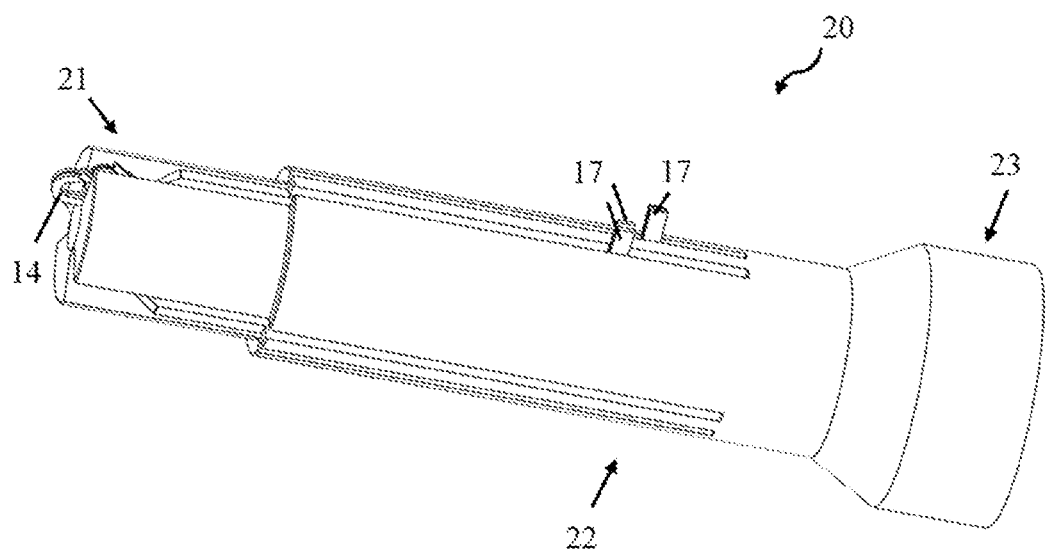
FIG. 10
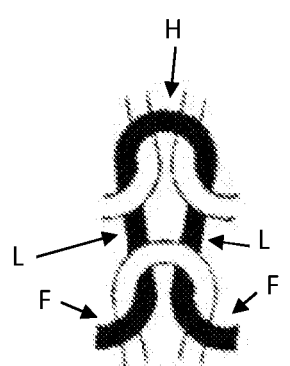 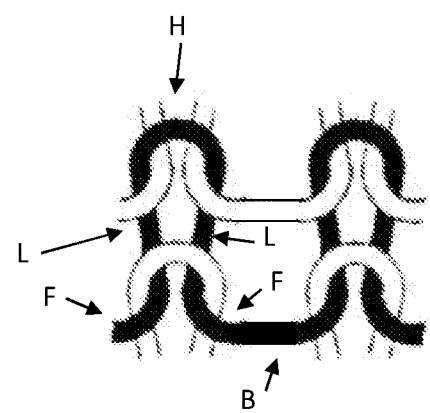
FIG. 11A          FIG. 11B

TUBULAR KNITTED STENTS

FIELD OF THE INVENTION

This invention relates to the field of knitted medical devices, more particularly to the field of tubular stents for use within a body, and to methods for producing them. These stents can be used in the human body and in animals. The stents have a high crimping ratio, which gives them the possibility to be used in different body lumens. The invention further relates to a method of producing a stent of this type. The invention is useful in particular in the field of health care, more particularly in the field of stenting body lumens.

BACKGROUND OF THE INVENTION

Tubular stents are used in various human body lumens to perform various functions. One of those functions is maintaining the opening of the lumen or for instance to strengthen or reopen body lumens such as blood vessels.

Several types of tubular stents exist commercially. There are expandable and self-expanding stents. Commonly, a stent is inserted in the lumen in the non-expanded form using either a balloon catheter or a delivery system. Balloon expandable stents are expanded by inflating a balloon at the deployment site. In the case of a self-expanding stent, the stent can than expand autonomously in situ. Self-expanding stents are in general made of metals with super elastic properties. This is normally the metal alloy nickel-titanium, named nitinol.

Two techniques are commonly used for producing nitinol stents. Either they can be made by laser cutting, starting from a nitinol tube, or they can be made by textile manufacturing processes such as knitting starting from nitinol wires, or ribbons or such.

The stents that are made by laser cutting, such as described for instance in US20070073374, have the advantage that they can be compressed to the diameter of the original tubing diameter or even smaller. This makes them insertable in many locations in the body.

Trade-offs between profile and performance have always been a significant issue for the design of implantable medical devices. This is a particularly important issue for stent and stent grafts of which many types need to be inserted through the femoral artery. The challenge in the past decades was to deliver stents via progressively smaller delivery catheters. The advantages offered by lower-profile devices are clear. Not only can patients with smaller access lumens be treated more optimally, but access site complications and overall procedural mortality rates are lower with smaller devices, and improve access options for the physician.

The stents made by laser cutting such as described for instance in US20070073374, exhibit a high bending stiffness, which is not favourable in zones of the human body where there is a lot of bending movement, such as the knee. Laser cut stents have also the disadvantage that producing long stents (up to 200 mm) takes much longer than for example knitting—see below.

The other possibility to produce nitinol stents is the textile manufacturing process. Most wire based stent designs on the market are braided stents, and only few stents are knitted stents. The stents that are made by knitting, such as described for instance in U.S. Pat. No. 6,221,099, have the advantage that they can have an almost infinite length and that they can exhibit a high zero axial stiffness range. However, they have the disadvantage of the crossing wires and therefore the corresponding higher wall thickness so that they can't be compressed to narrow diameters, which make them so far unsuitable for many surgical interventions.

US20130211496 also describes another possibility to further improve the properties of a circular knitted stent. The inventors claim to reverse the original internal side of the circular knit to the final outside side of the stent to smoothen the outside of the stent.

The two ways of producing nitinol stents described above have each their own disadvantages. This makes that at this moment, certain weakened body lumen stents to perform surgery do not exist. In these cases, the ideal stent must have a high length, must exhibit a high zero axial stiffness range, a high axial bending angle and must be able to have a crimping ratio up to 3.5 times its initial diameter.

SUMMARY OF THE INVENTION

An object of embodiments of the present invention is to provide a tubular knitted stent that can be made in any desired length, that can be crimped to a diameter necessary for most of the interventional procedures, that has a high angle in which it can axially bend and that has a high zero axial stiffness range. A knitted stent with these properties can be used for most of the vascular interventions. The above-described knitted stent can be used in particular for lumens where a lot of body bending movements occur.

The object named above is attained by a textile, for instance a knitted textile, according to embodiments of the present invention.

In a first aspect the present invention provides a textile, more particularly a knitted textile, which is tubularly knitted with wide knitting loops, in such a way that the knitting loop width to stent outer diameter ratio is bigger than 0.2 for at least one knitting loop, and optionally for all knitting loops.

It is an advantage of embodiments of the present invention that the tubular stents are knitted. The knitting process is an efficient manufacturing process, which can be carried out with an endless in practice very long-wire. This way, stents can be knitted continuously, and after manufacturing they can be cut to a desired length. The knitting can be such that the sent is immediately produced in a tubular form. This is especially advantageous compared to the formation of stents from mesh: the alignment and closure, e.g. welding such as laser-welding, of the mesh itself is a very time consuming process. Laser-welding processes are difficult to be automated. Moreover, integrally formed tubular structures, as in accordance with the present invention, with an endless wire, are advantageous over welded mesh, as the welded mesh always forms a weak point in the structure, and decreases flexibility of the stent.

In a second aspect the present invention provides a method of producing a knitted stent according to the first aspect of the invention. Hereto, a knitting head is used, being a cylindrical structure with a central bore for tubular knitted textile to pass through. The knitting head has needle slots designed to support and guide knitting needles. The method is described by the use of multiple knitting needles in at least one needle slot. With this technique a wider loop width can be obtained than when only using one knitting needle.

In a third aspect the present invention provides a method of producing a knitted stent according to the first aspect of the invention. The method is described by the use of a knitting technique called collapsing loops. In this technique the knitting head is made with a low number of slots. The material part, e.g. metal part, between the two slots of a slot pair is to large extent removed. By doing this, this will result in a single wide collapsing loop with the slot pair during knitting. By adapting the radial distance between two slots, it is possible to adapt the loop width of the final knit.

In a further aspect, the present invention also provides a knitting head for manufacturing a tubular knitted stent or stent graft for placement in a lumen or body passage. The knitting head comprises a plurality of longitudinally extending needle slots for supporting and guiding multiple knitting needles, needle slots of a subset being arranged closer to one another than to needle slots of another subset, and needle slots of a subset sharing an angular wedge recess. In a knitting head according to embodiments of the present invention, each needle slot may comprise at least one, and preferably a plurality of knitting needles.

The developments of the invention are described in the claims or below in connection with the description.

In a preferred embodiment of the present invention, the tubular knitted stent is made of one or multiple wires. In the most preferred embodiment of the present invention, the tubular knitted stent is knitted with two wires.

In a preferred embodiment of the present invention, the wires at the end of the stent do not have any sharp edges. When the stent consists of one wire, this can for instance be obtained by welding the wire to the end of the stent itself. When the stent consists of two or multiple wires, these wires can be bound or welded together.

In one embodiment of the present invention, the wires can be chosen from a wide range of materials, each with their own functions. A non-limiting exemplary list of materials is stainless steel, silver, nitinol, man-made polymeric yarns, polished wires, wires made by the above materials but with a radiopaque core, such as platinum or tantalum. However, in a preferred embodiment, nitinol wires are used for knitting the stent.

In one embodiment of the present invention, the thickness of the wire used to knit the stent has a diameter between 50 micrometre and 500 micrometre, making the wire durable enough for the application and making it possible to compress the knitted stent to an appropriate size for the physicians. In a preferred embodiment of the present invention, the wire has a diameter between 50 micrometre and 100 micrometre.

In one embodiment of the present invention, the tubular stent with one or more wires is knitted with loops that have a loop width to stent outer diameter ratio that is greater than 0.2. According to embodiments of the present invention, the stent outer diameter is the width of the tubular knitted stent when the tubular stent is non-compressed. The number of loops in each section of the tubular knitted stent is as such not defined (variable with an upper bound), but the loop width is.

In the context of the present invention, a "section" of the tubular knit refers to a longitudinally (axially) repeating unit forming the tubular knit. A section comprises two or more loops, with a defined, repeating loop height and loop width.

In the context of the present invention the "stent outer diameter" of the tubular knit is the outer diameter of the stent in a non-compressed or non-annealed form, measured from one radial end of the stent to another radial end of the stent, expressed in millimetre.

The tubular knit will in particular be used as a stent that is inserted into, for instance, but not limited to, arterial or venous blood vessels, more specifically for instance blood vessels that are present in zones in the body where a lot of bending movements occur. Furthermore, the use of the tubular knit stent is not limited to the use in human body, but can also be used for the same purpose in animals.

In a method according to embodiments of the present invention, the tubular knitted stent is made with the use of multiple needles in one knitting head slot that has larger needle slot widths. This method creates the possibility to have tubular knitted stents with loop widths that are wider. The wires that are used to knit the tubular knitted stent are taken up together by the multiple needles in one needle slot. Furthermore, in a preferred method according to embodiments of the present invention, these knitting needles are glued or welded together, so they can more easily act together.

In a method according to embodiments of the present invention, the tubular knit is made with the use of a knitting technique called 'collapsing loops'. This method creates the possibility to have a tubular knitted stent with loop widths that exceed a width of 0.2 times the stent outer diameter. To create these collapsing loops, the verge is removed between two needle slots one by one so that pairs of needle slots are created. One wire will be taken up by at least one knitting needle for each pair of slots so that instead of two different knitting loops, one 'collapsed' loop will be made. According to a preferred embodiment of the present invention, at least two knitting needles, one for each slot in a pair of slots, are used in at least one pair of slots, preferably for each pair of slots, for taking up one wire.

It has been found advantageous that the tubular knitted stents produced by the above-described techniques have a high zero axial stiffness range, which is advantageous once placed in the human body. Furthermore the stent can bend to a high extent without buckling, which is again of use once placed in the body lumen. This knitted stent is advantageous for the physician, since it can be compressed to the appropriate size because of its construction. Furthermore when it is compressed the stent exhibits almost no elongation behaviour, which is crucial for the interventionalist to perform correct surgery. Because of the design of the loops, the stent still has an appropriate radial strength.

The zero axial stiffness range (ZSAR) is defined as the range whereby the weft knitted stent can be compressed over a certain range at zero force. The range depends on the architecture (size, shape) of the knitting loops and bridges and is determined as follows:

Knitted stent is elongated and released-length L0, knitted stent is compressed and released-length L1. ZSAR is defined as $(L0-L1)/L0 \times 100\%$.

In one embodiment of the tubular stent, the tubular knit is reversed so that the original internal side of the tubular knit becomes the outside and vice versa. The surface now on the outside is smoother than the inside, which can be more advantageous to the patient.

BRIEF DESCRIPTION OF THE FIGURES

The invention will be further described, with reference to these accompanying figures.

FIG. 10 is a perspective view of the knitting head of FIG. 6 oriented differently and with two knitting needles inserted into each needle slot (only a few knitting needles are drawn for clarity).

FIG. 11A is a schematic illustration of a knitted loop.

FIG. 11B is a schematic illustration of 2 neighbouring knitted loops in accordance with embodiments of the present invention, distant from one another over the distance of a bridge.

DEFINITIONS

Figure 1:
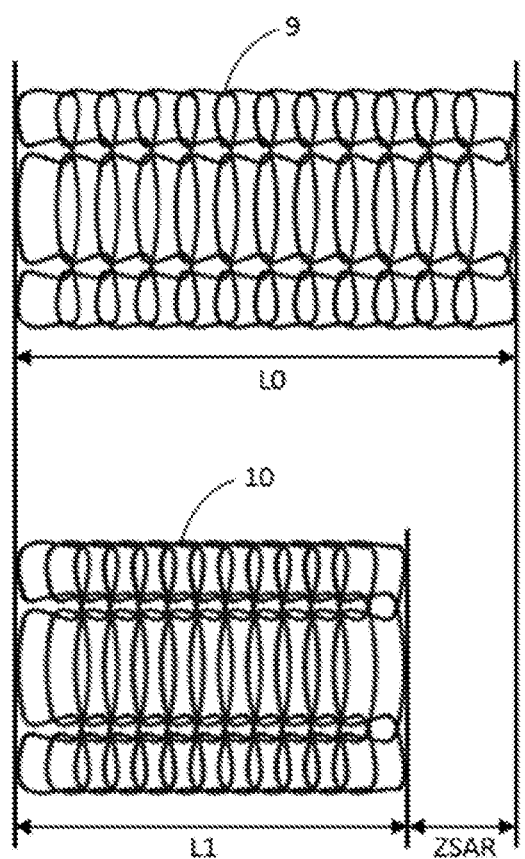
FIG. 1 shows the knitted stent in its elongated and released position and the knitted stent in its compressed and released position.

Knitting, according to the Handbook of Technical Textiles, Elsevier, can provide two different families of knitting structures, depending on the knitting process. Warp knitting is a method of making a fabric by making loops from each warp formed substantially along the length of the fabric. Weft knitting is a method of making a fabric by making loops from each weft thread that are formed substantially across the width of the fabric. It is characterised by the fact that each weft thread is fed more or less at right angles to the direction in which the fabric is produced. In the context of the present invention, weft knitting is used.

The present invention relates to formation of tubular stents. A tubular stent in the context of the present invention is laterally closed, i.e. it is closed on its longitudinal circumference, and has open end portions, so as to form an open tube. This is different from structures formed from flat structures rolled into a spiral-like structure before use. The tubular stents in accordance with embodiments of the present invention are knitted, hence with circumferentially closed is meant that no slits, e.g. slits in the axial direction, are present. Holes are present in between two loops or two bridges.

The stent outer diameter of a tubular knitted stent is defined in the context of the present invention as the length of a straight line lying in a cross-sectional plane of the tubular stent and passing through the centre axis of the stent, having its endpoints lying on a projection of the radially outward oriented edge of the wires onto this cross-sectional plane.

As defined in the book "Knitting Technology: A Comprehensive Handbook and Practical Guide", the needle loop is the basic unit of knitted structure. An example is illustrated in FIG. 11A. When tension in the fabric is balanced and there is sufficient take-away tension during knitting, the loop is an upright nose formed by at least one needle hook. It consists of a head (H) and two side limbs or legs (L). If the head is placed horizontally, the side limbs, which are located at either side of the head, are ascending and descending, respectively. At the base of each leg is a foot (F), which meshes through the head of the loop formed at a previous knitting cycle, usually by that same needle. In general, the yarn passes from the foot of one loop into the foot and leg of the next loop formed by it. In the context of the present invention, however, feet of two neighbouring loops are separated from one another over a distance called a bridge (B), as illustrated in FIG. 11B. In the context of the present invention, the distance between neighbouring loop feet is higher than what is conventionally known. In the context of embodiments of the present invention, the loops may be substantially block-shaped. The loops may be arranged in a plurality of columns along an axial direction of the stent or stent graft.

The loop height of a knitting loop of a tubular knitted stent is defined in the context of the present invention as the distance of the lower edge of the wire from the loop head to the upper edge of a wire from the loop head below if viewed along an axial direction of the stent.

The loop width of a knitting loop of a tubular knitted stent is defined in the context of the present invention as the longest distance between the two ascending, inner bent portions of the loop, defined as legs hereinabove.

The bridge width of a knitting bridge of a tubular knitted stent is defined in the context of the present invention as the longest distance between the two descending, inner bent portions of the bridge, i.e. the ankles at the loop basis or thus the feet, which connect the bridge to its adjoining loops.

The crimping ratio of a tubular knitted stent in the context of the present invention is defined as the diameter of the knitted stent as is divided by the diameter of the stent when it is crimped.

DETAILED DESCRIPTION

In the following, reference is made to FIG. 1 to FIG. 4. When in the following a tubular knitted stent is described, it is assumed that a tubular knitted stent graft may be used interchangeably with the tubular knitted stent, unless stated otherwise.

Figure 2:
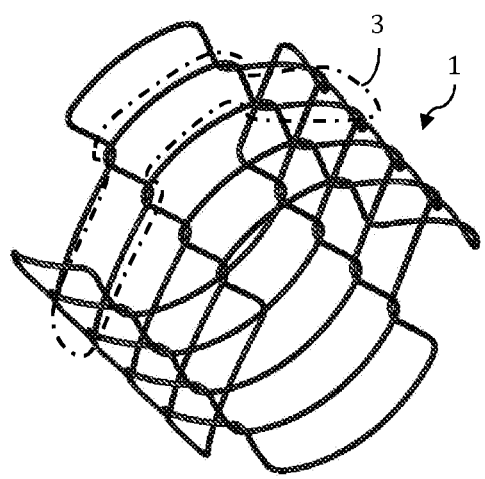
FIG. 2 shows a tubular knitted stent with five sections in which multiple loops and bridges are visible.
Figure 3:
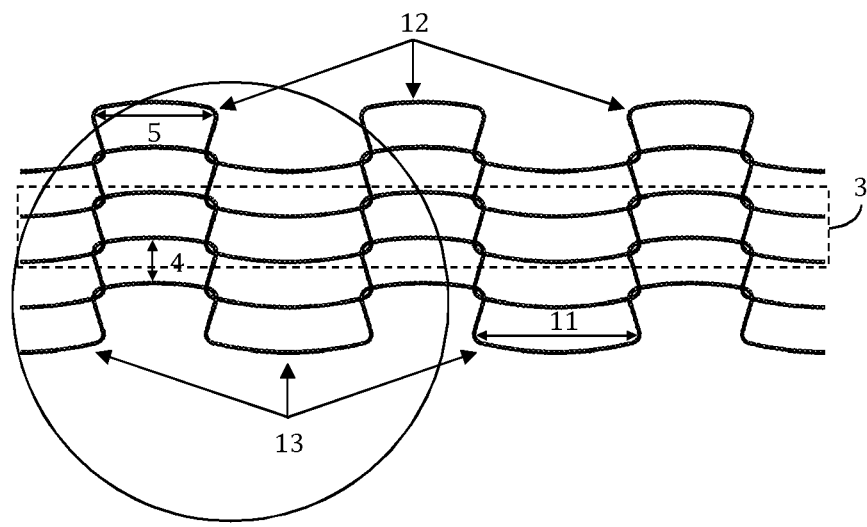
FIG. 3 shows a 2D model of the knitted stent with the definition of the loop height and the loop width. Between the loops one can find bridges with a well-defined bridge width. A section is one part of the stent. A number of loops and bridges together define a section of the tubular knitted stent.
Figure 4:
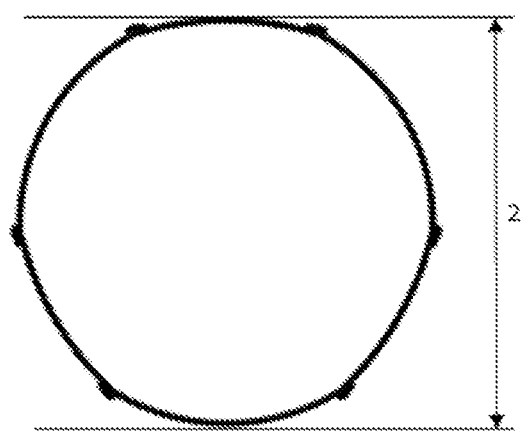
FIG. 4 shows a top view of a stent according to embodiments of the present invention, illustrating the stent outer diameter.

FIG. 2 shows a perspective view of a tubular knitted stent 1. A knitting pattern is repeated five times, in the embodiment illustrated, along the longitudinal or length axis of the tubular knitted stent 1 and each repeated element of the pattern is referred to as a "section" 3 as also illustrated in the flattened view of a part of the tubular knitted stent in FIG. 3. A section 3 is comprising a sequence of bridges 13 and loops 12 that extend around the tubular knitted stent's 1 circumference. The bridges 13 and loops 12 have a bridge width 11 and loop width 5, respectively, in accordance with the definitions mentioned above. The loops 12 are further characterized by their height 4. As illustrated in FIG. 4, the tubular knitted stent 1 has an outer diameter 2 in a plane of cross-section, measured from end point to end point along a straight line crossing the centre point of the tubular knitted stent 1 as seen in the plane of cross-section. The end points correspond to the points at which the straight line intersects the outer rim of the knitting wire.

According to embodiments of the first aspect of the present invention, a tubular knitted stent or stent graft 1 comprises loops 12 having each a loop width 5 such that in an uncompressed state 9 of the stent or stent graft 1, the loop width 5-to-stent outer diameter 2 ratio is greater than 0.2. In a preferred embodiment of the present invention, each knitting loop 12 has a loop width 5 that is larger than 0.4 times the stent outer diameter 2. A selected loop width-to-stent outer diameter ratio is also defining an upper limit on the maximum number of knitting loops 12 placed around the tubular knitted stent's 1 perimeter in each section 3. In matters of radial compressibility of the tubular knitted stent 1, the number of loops 12 per section 3 is of great influence. In preferred embodiments of the present invention, a small number of loops 12 in each section 3 is chosen, i.e. smaller than the maximum number of loops 12 imposed by the loop width-to-stent outer diameter criterion, as this is positively affecting the compression possibility of the tubular knitted stent 1 down to the desired target diameter. This way crimping/radial compression ratios preferably higher than two, and even more preferably higher than three, may be achieved. Nonetheless, the final compressed or crimped stent outer diameter targeted may, of course, depend on the particular application.

In particular embodiments of the present invention, not all loops 12 of a section 3 have the same loop width 5. Different loops 12 may have a different loop width 5. In preferred embodiments of the present invention, all loops 12 of a section 3 have the same loop width 5, resulting in symmetrical sections 3. It is of benefit to provide symmetrical sections 3 as this ensures good local body lumen support (e.g. local artery support). If one loop 12 of section 3 happens to be much smaller than the others, large bridge widths and a bad local artery support would be the consequences. Symmetrical sections 3 also ensure that good crimping ratios are obtained, as increased overlap between large bridges 13 is avoided. An additional advantage of symmetrical sections 3 is that a more uniform block shape factor (BSF) and therefore a larger ZSAR is achieved, whereas having a too small loop in a section 3 implies a larger BSF for this too small loop, which would negatively impact the ZSAR.

The tubular knitted stent or stent graft 1 can, due to the larger loop width-to-stent outer diameter ratio, be compressed or crimped in a radial direction to an appropriate size for interventional procedures, e.g. a size suitable for placement on a catheter or a size suitable for introducing it into a hollow body lumen by means of a stent delivery system. Crimping may involve crimping on an inner cylindrical support structure. It is an advantage of embodiments of the invention that a greater loop width-to-stent outer diameter ratio allows for fewer but wider loops 12 in each section 3 so that a high compression or crimping ratio is obtained under a radial compression or crimping action. Other advantages related to fewer but wider loops 12 in each section 3 in accordance to the greater loop-width-to-stent outer diameter ratio include non-overlapping ankles (the bent portion located at the loop basis) during crimping of the tubular knitted stent 1, a small crimped wall thickness, the feasibility of smaller loop openings leading to better scaffolding properties, and a high radial stiffness of the released, uncrimped tubular knitted stent 1 that prevents an incomplete apposition of the stent to the vessel wall.

FIG. 1 is a side view of a knitted stent 1 and illustrates how, under the influence of a compressive, axial force, the knitted stent 1 is changed from an elongated, uncompressed state 9 of length L0 to a compressed state 10 of shorter length L1 when released. It is an advantage of embodiments of the invention that the knitted stent is characterized by a range of compressed state 10 lengths L1 which are obtained by applying a compressive force that is substantially zero. For such lengths L1 a zero stiffness axial range, ZSAR, may be defined as follows:

$$\pm ZSAR = \frac{L0 - L1}{L0} \cdot 100\%.$$

A negative ZSAR value is the result of applying, along an axial direction, a substantially zero stretching force, instead of a substantially zero compressive force, to the knitted stent 1, such that it is changed from an elongated, uncompressed state 9 of length L0 to a stretched state 10 of longer length L1 when released. The absolute ZSAR value, according to particular embodiments of the present invention, is particularly high, e.g. an inherently high ZSAR value of 50% may be obtained, meaning that the axial compression or stretching resistance is zero for a 50% change in axial length, i.e. L1=±0.5 L0. A high absolute ZSAR value, and also a high zero bending stiffness range (ZBSR) value, is of advantage since it allows for a substantially free movement of the body lumen without any hampering resistance of the stent 1. As a consequence the body lumen experiences tolerably little or no injuries and the tubular knitted stent 1 installed therein benefits from very high fatigue resistance and is highly compliant with both axial and bending deformations of the body lumen without failing to fulfil its lumen support function.

A knitted stent 1 according to embodiments of the invention may be knitted with one or more wires. Preferably, a knitted stent is knitted with two wires. The wires are preferably made of a material which is sufficiently biocompatible. The latter characteristic allows for knitted stents that cause no or only tolerably low allergic body reactions. The one or more knitted wires are preferably made of a super elastic shape memory alloy that enables the stent to be compressed and to be kept in its compressed form 10. The materials preferably used for the wires are specific nickel-titanium alloys, also known as nitinol wires. Other materials that may be used for one or more wires are for example, without being limited thereto, stainless steel, silver, man-made polymeric yarns. The wires that are used to knit the stent have preferably a cross-sectional diameter between 50 micrometre and 500 micrometre. In even more preferred embodiments of the present invention, the cross-sectional diameter is ranging between 50 micrometre and 100 micrometre.

An exemplary tubular knitted stent 1 according to embodiments of the present invention has a stent outer diameter 2 of four to eight millimetre and is for instance knitted with two wires, each having a cross-sectional diameter between 50 micrometre and 150 micrometre. A cross-sectional wire diameter between 80 micrometre and 120 micrometre is even more preferable.

The cross-sections of the wires may have any shape, but a circular cross-sectional profile is the most preferred shape. When knitting with two or more wires, these wires may have the same or, alternatively, may have two or more different cross-sectional diameters within the aforementioned ranges. This may be advantageous regarding the radial strength of the tubular knitted stent and the crimping ratio of the tubular knitted stent.

Furthermore a tubular knitted stent 1 according to embodiments of this invention may have an inherently high zero bending stiffness range. When bending the tubular knitted stent 1, preferably no lumen reduction occurs for bending angles less than 130°. Even at bending angles close to 180°, the maximum lumen reduction is less than 20%. The tubular knitted stent 1 exhibits these compelling properties because of the specific loop width 5 and the design of the knit.

In the following reference will be made to FIG. 6 to FIG. 10.

Figure 6:
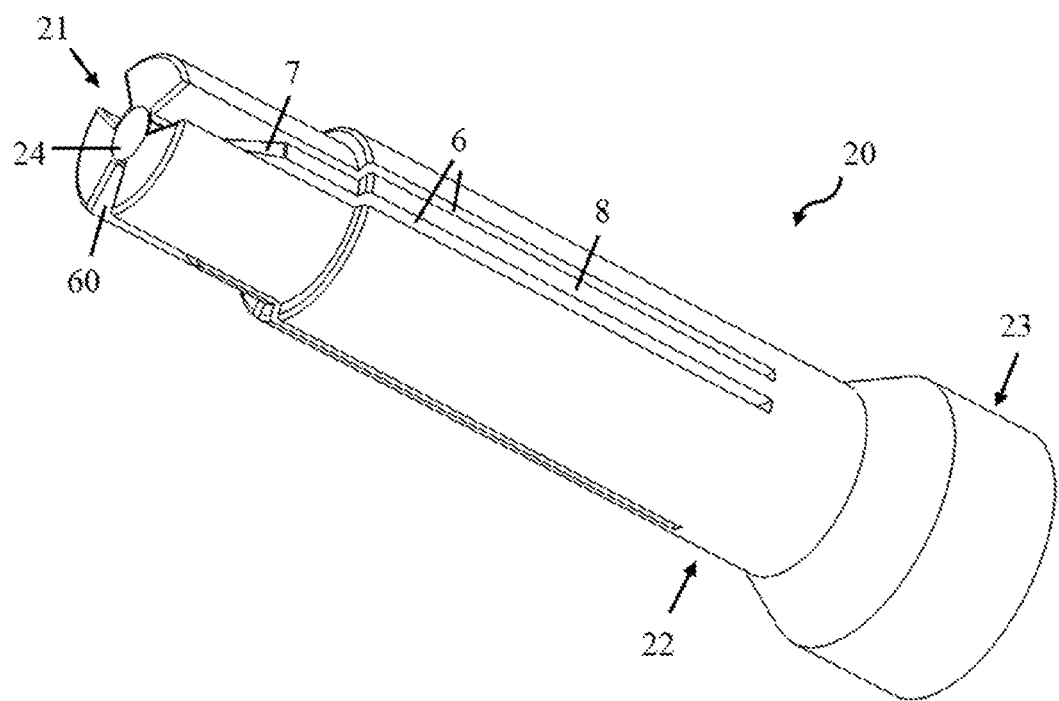
FIG. 6 shows a perspective view of a knitting head used for knitting tubular stents according to embodiments of the present invention, having three knitting needle slot pairs for supporting and guiding one or more knitting needles, and a top of a verge between adjacent needle slots being removed.
Figure 7:
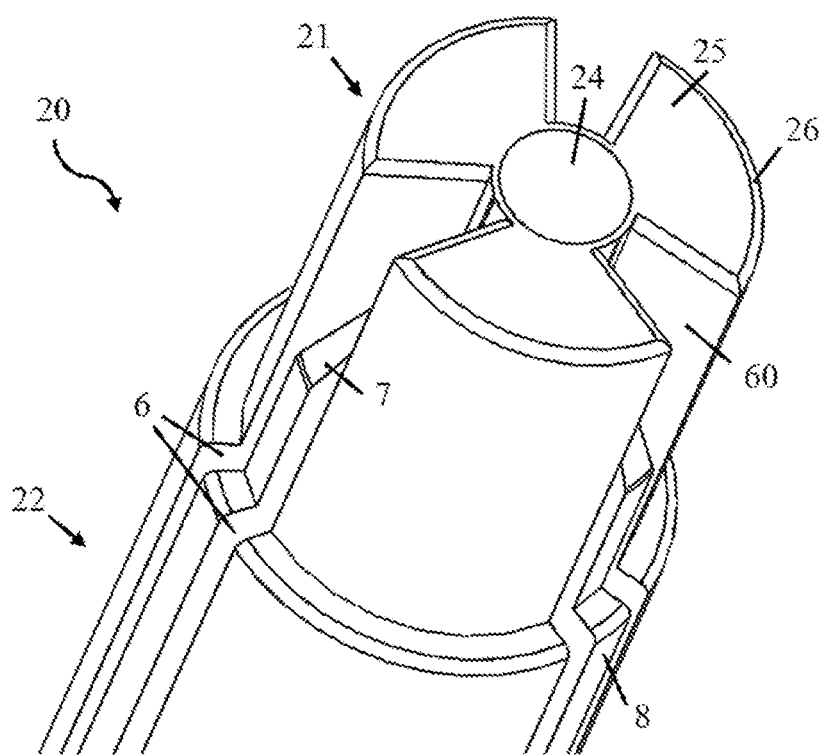
FIG. 7 is a detailed view at a different orientation of the front section of the knitting head as shown in FIG. 6.
Figure 8:
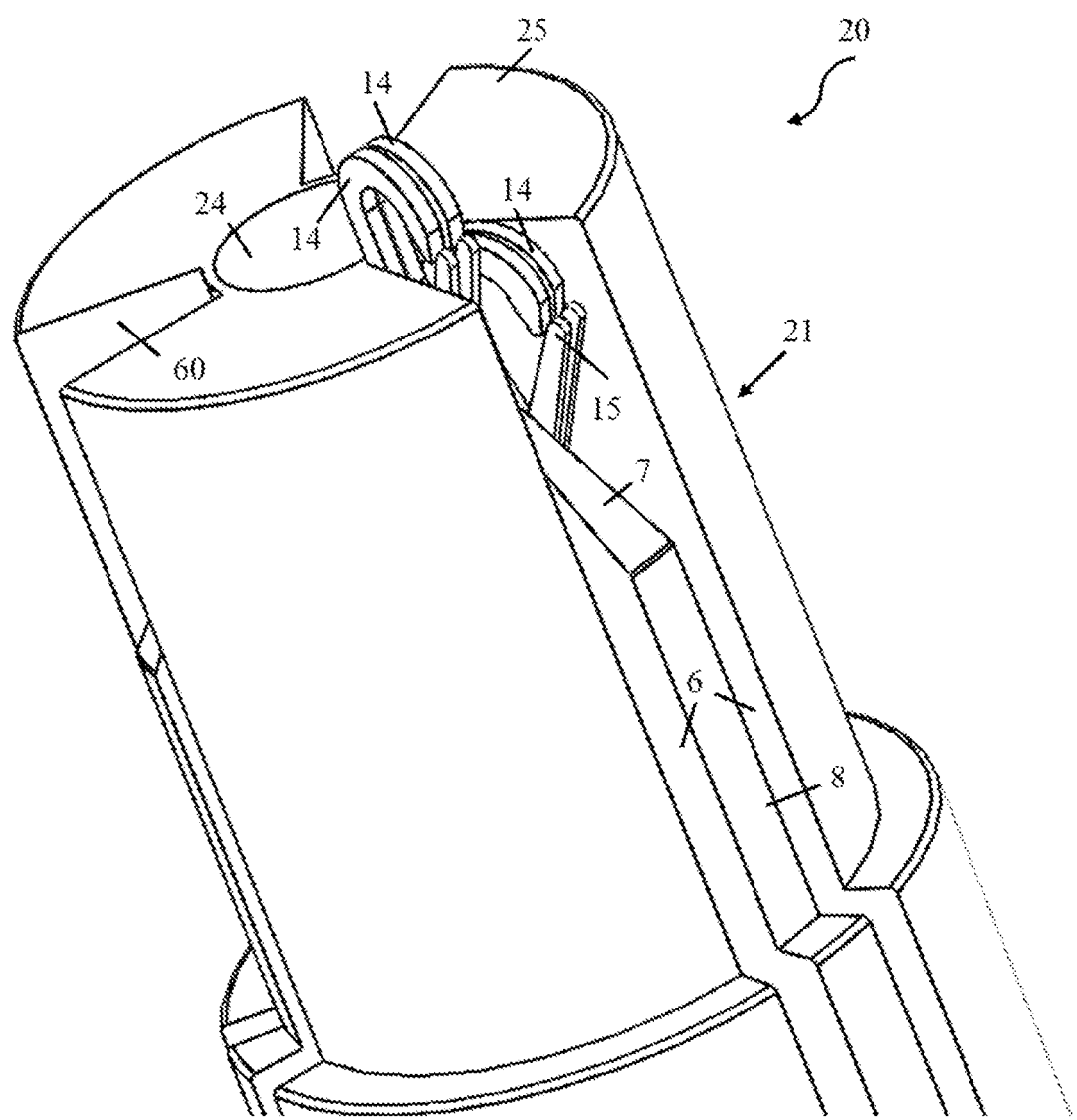
FIG. 8 is a detailed perspective view of the front section of the knitting head as shown in FIG. 6, but with two knitting needles inserted into each needle slot (only a few knitting needles are drawn for clarity).
Figure 9:
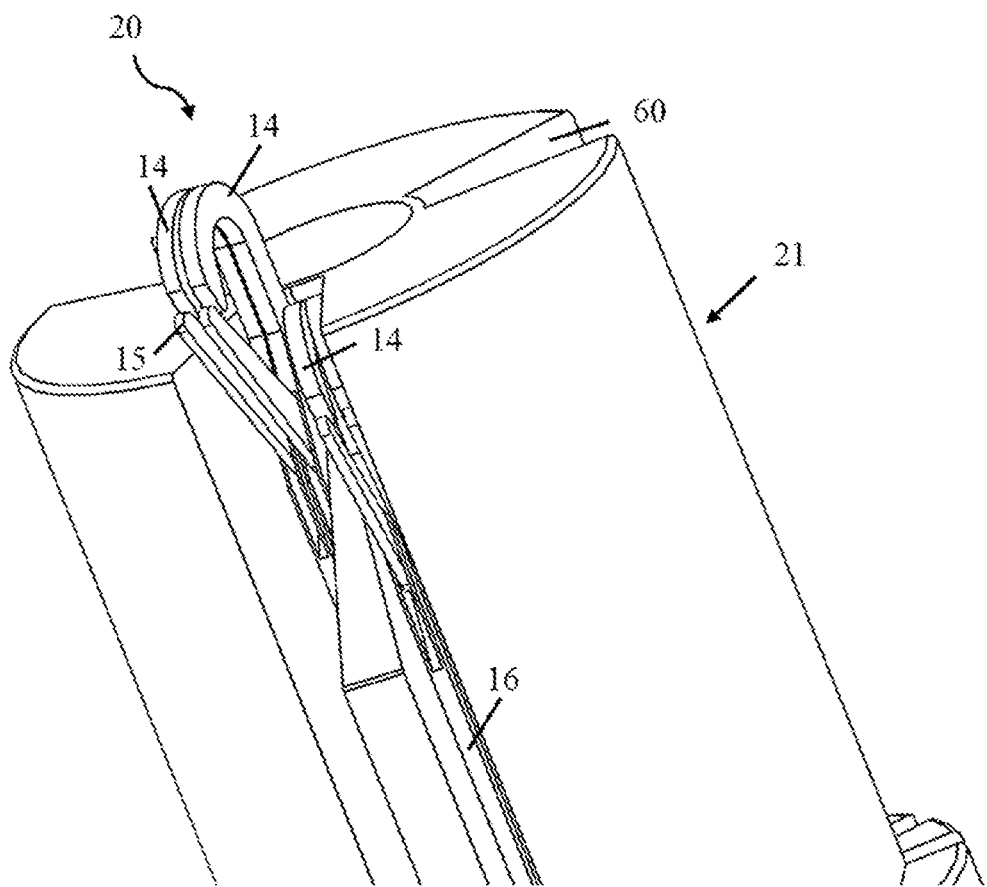
FIG. 9 is a detailed perspective view of the front section of the knitting head as in FIG. 8, but shown at a different angle.

In embodiments of a second aspect of the invention, a method for knitting a tubular stent according to the first aspect of the invention is provided, in which two or more knitting needles 14 are placed within each needle slot 6 of a knitting head. FIG. 6 is a perspective view of a knitting head 20 which may be used for such a method. The knitting head 20 is typically shaped as a cylinder with a central bore 24 and may comprise several sections, e.g. a rear section 23, a middle section 22, and a front section 21. These sections 21, 22, 23 are preferably formed as integral parts of the knitting head 20. The rear section 23 of the knitting head 20 may have a wider cross-section than the other sections to provide good means to secure and fasten the knitting head 20 on an external support, which makes sure that a good uniformity of the loops and loop wales is achieved during the entire knitting process. On its outside, the knitting head 20 is provided with longitudinally extending slots 6 for supporting and guiding the multiple knitting needles 14. Two adjacent needle slots 6 are separated by slot walls 8. The needle slots 6 may be machined directly into the knitting head 20. In the particular embodiment illustrated in FIG. 6 through FIG. 10, there exist six needle slots 6 in total, whereby needle slots 6 are arranged in pairs closer to one another. FIG. 7 is a closer perspective view of the front section 21 of the knitting head 20. The three slot pairs are formed as angular wedges 60 removed from the bulk in a front section 21 of the knitting head 20. Adjacent angular wedge recesses 60 are divided by angular bulk sections 25 of the body of the knitting head 20. In a lower half of the front section 21 of the knitting head 20, each of the angular wedge recesses 60 transitions into a plurality, in the example illustrated e.g. two, substantially identical groves, which, in their extension along the middle section 22 of the knitting head 20, form a subset, e.g. a pair, of needle slots 6. This transition between angular wedge recesses 60 and needle slots 6 is realized by removing the top of the verge 7 of slot walls 8, whereby the verge 7 may be removed gradually, e.g. by shaping the top of the verge 7 as a chamfer. In particular embodiments of the present invention, there may be as little as three of those angular wedge recesses 60 present in the front section 21 of the knitting head 20 for obtaining only a small number of loops 12 in each row 3 of the knitted stent 1, e.g. only three loops. The angular extent of the angular wedge recesses 60 also determines the width of a knitted loop 12, which, as illustrated in FIG. 7 to FIG. 9, is not small but comparable to the width of bridges 13 determined by the angular extent of the bulk sections 25. An edge of the front section 26 of the knitting head 20 may be bevelled to avoid injuries, as may be the transitions between front section 21 and middle section 22, and between middle section 22 and rear section 23 of the knitting head 20. The needle slots 6 as well as the angular wedge recesses 60 are preferably provided with the same depth in a radial direction of the knitting head, e.g. a radial direction of a cylindrical knitting head 20 defined by a point on its circumference and its centre. This depth is preferably chosen as large possible, e.g. as large as the structural identity of the thin wall separating the bore 24 from the needle slots 6 and the angular wedge recesses 60 allows, such that knitting needles 14 may be brought as close as possible to the central bore 24 through which the knitted weft is guided on a fixture. This advantageously reduces the length of the path along which a force is applied to the knitting needles 14, hence reducing the work performed on them and also enabling direct knitting onto a fixture. Moreover, this is reducing the wear of the needles 14 or the guiding and supporting needle slots 6. To further reduce wear of the needles 14 and needle guiding means, and to make the replacement of knitting needles 14 easier, said knitting needles 14 may also be inserted into supporting and guiding needle bars which are connected to the knitting head 20.

FIG. 8 and FIG. 9 show the front section 21 of the knitting head 20 with knitting needles 14 inserted into the needle slots 6. For the sake of better visibility only four knitting needles 14, arranged into two pairs of two needles each, are drawn, but more knitting needles may be inserted in the same manner into the remaining empty needle slots 6. Furthermore, it is possible to have more than two knitting needles 14 placed in each individual needle slot 6. The multiple knitting needles 14 of a pair of adjacent needle slots 6 are not separated by a slot wall 8 in a front section 21 of the knitting head 20. With the top of the verge 7 removed, it is indeed possible to form collapsing loops 12 in the regions of angular wedge recesses 60 without the hindrance of projecting parts of the knitting head 20, e.g. projecting slot walls 8. To be capable of knitting small stents 1, the hooks of the knitting needles 14 are preferably chosen as small as possible. In preferred embodiments of the invention, latch needles 14 may be used for fast knitting of the tubular stent 1. For latch needles 14, a latch 15 allows taking the wire thread in an open configuration and retaining it within the hook in a closed configuration. The knitting needles 14 are provided with an elongated stem 16 whereto the hook and the latch are connected, the latter typically comprising latch blade and latch spoon.

Butts 17 may be formed as projecting parts of the elongated stem 16 of the knitting needles 14, as shown in the perspective view of FIG. 10. Whereas the elongated stem 16 and a tail section of the knitting needles 14 are hidden inside the needle slots 6, the butts 17 may be protruding from needle slots in a middle section of the knitting head 20, thereby providing steering means that enable the sliding movement of the knitting needles 14 under a knitting operation; the sliding movement typically is a repeated up and down movement of the knitting needles 14 in their respective guiding needle slots 6. When a knitting operation is carried out, the butts 17 may typically be located in cam tracks of a cam cylinder that may be rotating relative to the knitting head 20. The particular shape of the cam tracks then brings about a change in the height positioning of the knitting needles 14 such that descending and ascending former loops 12 are triggering the opening and the closing of the latch 15.

The multiple knitting needles 14 of each needle slot 6 act in unison; this effect is reinforced by attaching, e.g. gluing or welding together, the lower parts of the knitting needles 14 within the same needle slot 6. In preferred embodiments of the second aspect of the present invention, the method comprises a knitting step for knitting of the tubular stent 1 according to embodiments of the first aspect of the present invention, whereby the knitting is performed directly onto a fixture. The fixture and the knitted weft (not shown) are moved through the bore 24 of the cylindrical knitting head 20. The fixture preferably has a cylindrical shape, but various other shapes are possible, e.g. fixture shapes having conical or biconical segments, fixtures with a hexagonal or elliptical cross-section, etc. More complex fixture shapes have the advantage that stents with domed or conical segments are readily available through the direct knitting onto the fixture, resulting in an improved conformability of the tubular knitted stent 1 to the body lumen. Alternatively, the fixture may be conceived in a modular way with definite, pre-shaped modules being added and removed in successive steps as long as the knitting process continues. The fixture may be connected to a guiding mechanism, e.g. a rail-like guiding mechanism, that prevents the fixture from deviating laterally or from engaging into a rotational movement, both leading to irregularities during the knitting process. Moreover, the guiding mechanism enables knitting of stents 1 which have their wales aligned parallelly to the fixture axis. Weights may be added at one side of the fixture for pulling it steadily through the knitting cylinder 20.

Figure 5:
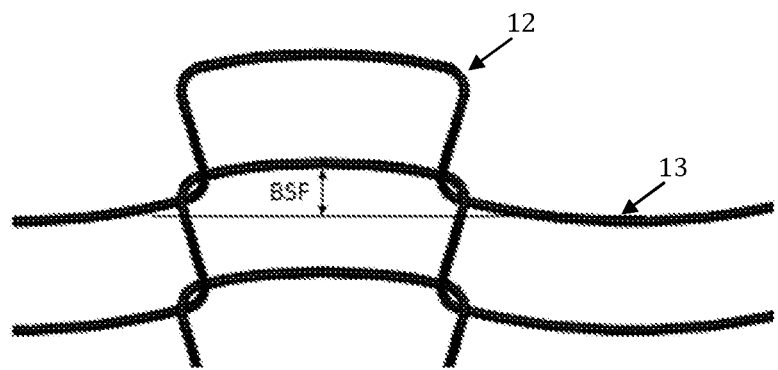
FIG. 5 shows part of a 2D model of the knitted stent with the definition of the block shape factor (BSF).

Benefits of the above-described direct knitting on a fixture for shape setting of the knitted weft or stent include avoiding the formation of irregularities during the knitting process, and avoiding the time-consuming and delicate step of transferring and expanding the knitted weft or stent onto a shape setting element on which the transferred, knitted weft or stent is undergoing a heat treatment for permanently fixing its shape, obtaining directly substantially block-shaped loops 12. Symmetrical block-shaped loops 12 exhibit large absolute ZSAR values and are therefore preferred loop shapes. FIG. 5 show nearly block-shaped loops 12 and defines a block shape factor, BSF, as a measurable quantity, i.e. as the (axial) height distance between facing wire edges of a loop belonging to a first section and an adjacent bridge belonging to the next section. In preferred embodiments of the invention, the BSF is less than 0.5 mm. The BSF can be optimized by an appropriate choice of the wire tension and the pulling weight of the fixture, by minimizing the needle slot 6 inner diameter, and by minimizing the gap between the fixture outer surface and the knitting cylinder inner surface. Furthermore, the formation of loop 12 of very small height 4 is possible through the directly knitting on a fixture. Setting of the heights of the knitting cams influences the obtained loop heights 4. As a consequence of smaller loop heights 4 a more homogenous scaffolding of the body lumen can achieved and the radial stiffness of the tubular knitted stent is increased.

To reduce the loop height 4, knitting needles 14 with a small hook are preferred. If, by using such knitting needles, the number of loops 12 in each section 3 is reduced to less than four in accordance to particular embodiments of the first aspect of the present invention, the resulting bridges 13 may be too wide, e.g. leading to loop width-to-bridge width ratios smaller than 0.6. To meet the requirement of a loop width-to-stent outer diameter ratio greater than 0.2, wider loops 12 are indispensable. In response thereto, knitting cylinders with wider needle slots 6 may be manufactured so as to fit two or more knitting needles 14 into a single slot 6 according to embodiments of the second aspect of the present invention. The loop width 5 than grows linearly with the number of knitting needles 14 per widened needle slot 6.

In some cases it may be desired to further increase the loop width 5 and one therefore has to overcome the limited loop width obtainable by above method of arranging multiple knitting needles 14 side by side in a needle slot 6. Indeed, only a limited angle of the knitting cylinder can be covered by this method.

Embodiments of the third aspect of the present invention provide a method according to which neighbouring loops 12 are capable of merging with each other thereby forming one new and wider loop 12. The two coinciding loops originate from a pair of needle slots 6 machined into the knitting head 20 in close angular proximity (e.g. 20 degrees angular separation) to each other, whereas two pairs of needle slots are farther apart (e.g. 120 degrees angular separation). If the top of the verge 7 of a slot wall 8 separating the two, paired needle slots 6 is partly removed, a single wide loop 12 results during the knitting process. Much wider loop widths 5 are obtained by this method, whereby the particular loop width 5 is determined to a large extent by the angular width of the partly removed verge 7 between the needle slot pair. It is possible to combine the two above described methods, corresponding to the second and third aspect of the invention, by providing a knitting head 20 into which pairs of needle slots 6, each wide enough for fitting single or multiple knitting needles 14, have been machined and the top of the verge 7 of slot walls 8 in between them has been removed, and by arranging either one single needle or multiple knitting needles 14 into each needle slot 6. Such a combination allows the formation of very few, extremely wide knitting loops 12 in each section 3 of the tubular knitted stent 1 in agreement with the embodiments of the first aspect of the present invention. Alternatively, it is also possible to use less knitting needles 14, e.g. only a single needle per slot pair, and still yield collapsing loops by virtue of the partly removed verge 7 between slot pairs.

A tubular knitted stent 1 produced by any of the two methods described above may be reversed according to particular embodiments of the present invention, such that the knitted inner side becomes the final outer side of the tubular knitted stent 1. This decreases the surface roughness of the tubular knitted stent 1 and may, for instance, be of advantage in applications in which lesions to the body lumen need to be kept minimal. For reasons inherent to the knitting process, the knitted outer side of a tubular knitted stent 1 will be rougher than the knitted inner side. A reversed tubular knitted stent 1 may show additional desirable properties, such as a higher radial stiffness and a higher, angularly homogenous pinching stiffness.

To turn the tubular knitted stent 1 inside out, an extra wire may be threaded through the end loops 12 of the tubular knitted stent 1, whereby the tubular stent 1 is positioned on a stiff tube. When the extra wire is pulled by its ends through the supporting tube, the tubular stent 1 progressively moves forward on the tube and subsequently is pulled through the interior of the tube thereby reversing its orientation, viz. the inner side becomes the outer side and vice versa. An additional shape setting heat treatment may follow the reversal step so as to stabilize the stent's shape and to obtain good super elastic properties. During such a shape setting heat treatment the reversed, tubular knitted stent 1 is typically positioned onto a metal tube with or without a particular wall profile.

Furthermore, it is possible, according to particular embodiments of the present invention, to provide the tubular kitted stent 1 with a higher degree of radiopacity. This may be achieved by the selection of one or more special, radiopaque wires for knitting. Non-limiting examples of such radiopaque wires include tantalum or platinum wires, NiTi wires having a platinum core, NiTiPt or NiTiPd wires, etc. Alternatively, radiopaque elements may be added to the tubular knitted stent 1, e.g. by crimping tantalum beads to one or both ends of the stent 1.

According to particular embodiments of the present invention, the tubular knitted stent 1 may be provided as an unravelling stent or a non-unravelling stent. An unravelling stent has the advantage that it can be placed into a body lumen only temporarily and is removed at a later time. The unravelling of the stent 1 typically involves undoing the loops 12 of the sections 3, one loop 12 at a time and section after section. Means to facilitate the unravelling action may include the attachment of easy to grip beads or balls to the free wire ends on one or both sides of the tubular knitted stent 1, e.g. by crimping or welding, or providing wire ends extending out on one or both sides of the tubular knitted stent 1. To avoid premature unravelling of the tubular knitted stent 1, e.g. before properly positioning the stent 1 inside the body lumen, it is possible to provide the tubular knitted stent 1 with an unravelling blocking means. This blocking means may comprise one or more extra wires or strands that are threaded through several or all of the end loops 12 at one or both ends of the tubular knitted stent 1. Those extra wires may be removed again once the stent 1 is in its final position, prior to the unravelling step. Alternatively, instead of using extra wires or strands for threading, the same one or more wires used for knitting the tubular stent 1 may be used for that purpose.

The knitted tubular stent or stent graft 1, according to some embodiments of this invention, is compressed 10 before being inserted into a body lumen. This may be achieved by crimping the uncompressed 9 tubular knitted stent onto a restraining tube, e.g. a restraining silicon tube, in a first step, and drawing the crimped knitted tubular stent 1 on its restraining support tube into the hollow of a cylindrical tube of reduced inner diameter in a second step, whereby the reduced inner diameter is reduced in size with respect to the tubular knitted stent's 1 outer diameter 2 in its uncompressed state 9. The hollow cylindrical tube may, for example, be a stent delivery system, which then is positioned inside the body lumen. Crimping is typically done in a cooled state at temperatures below the memory transition temperature of the shape memory alloy used for the knitting wires in the stent 1. That way it is ensured that the expanded stent 1 inside the warmer body lumen, at temperatures above the memory transition temperature of the shape memory alloy, will only memorize its expanded state in the lumen. After removal of the ensheathing, cylindrical tube, the tubular knitted stent 1 expands to its initial knitted outer diameter 2. Self-expanding nitinol stents are usually oversized by at least 0.5 mm-1 mm to ensure contact with the body lumen wall and prevent migration. Once the tubular knitted stent 1 is deployed, it exerts a continuous force upon the vascular wall, termed chronic outward force (COF). Alternatively, a tubular knitted stent 1 which is not self-expanding, e.g. a stent which is not made from a shape memory alloy material, may be brought in contact with the vessel interior wall by means of an expandable balloon which is inflated at the deployment site of the stent and which plastically deforms the stent until it is exerting enough pressure on the vessel interior wall.

Example

The invention will be further described by means of a non-limitative example.

Two nitinol wires, purchased from Ford Wayne Metals, with the first having a diameter of 90 micrometre and with the second having a diameter of 100 micrometre are knitted using a tubular knitting head including three pairs of needle slots 6. Moreover, two knitting needles 14 are present in each single needle slot 6.

The so-produced tubular knitted stent 1 has a stent outer diameter 2 of 6 mm. The tubular knitted stent 1 is made of sections 3, each comprising three loops 12. The loops 12 in the sections 3 have a loop width 5 of 2.6 mm and a loop height 4 of 1.1 mm. This results in a loop width-to-stent outer diameter of 0.43, which is indeed larger than 0.2, in accordance with the claimed invention.

A tubular knit may be produced at infinite length and thereafter be cut into independent tubular knitted stents 1, each having a particular length, e.g. a tube length of 20 centimetre. The obtained tubular knitted stents 1 exhibit almost no axial compression resistance until an axial compression of the tubular knitted stents 1 reduces their axial length to 50% of their initial axial length.

The ends of the nitinol wires used for knitting the tubular stent 1 are typically welded together on both sides of the tubular knitted stent 1, so that there are no sharp edges present. Laser welding is typically used as a welding technique for welding together the knitted wire ends.

Because of its specific loop geometry and loop arrangement, the tubular stent 1 knitted in this way can be compressed to a diameter of 1.6 mm or even smaller. Hence, it is possible to draw such a crimped tubular knitted stent 1 into a 6 Fr catheter.

The invention claimed is:

1. A tubular knitted stent or stent graft for placement in a lumen or body passage, the stent or stent graft being compressible and having a compressed and a non-compressed outer diameter, the stent or stent graft having knitted loops each having a loop width,
    wherein at least one knitted loop is characterized by a loop width to non-compressed outer diameter ratio larger than 0.2.

2. The tubular knitted stent or stent graft according to claim 1, wherein the loop width to non-compressed outer diameter ratio is larger than 0.2 for each knitted loop.

3. The tubular knitted stent or stent graft according to claim 1 or claim 2, wherein the loop width to loop height ratio is larger than 2.0.

4. The tubular knitted stent or stent graft according to claim 1, the stent or stent graft having a predetermined number of loops on a circumference of the stent or stent graph,
    wherein the pre-determined number of loops is less than four.

5. The tubular knitted stent or stent graft according to claim 1, wherein the loops are substantially block shaped, as measured by a block shape factor BSF, the block shape factor BSF being less than 0.5 mm.

6. The tubular knitted stent or stent graft according to claim 1, wherein the stent or stent graft non-compressed outer diameter is 8 mm or smaller, and wherein the stent or stent graft can be compressed to a factor 4 or more.

7. The tubular knitted stent or stent graft according to claim 1, wherein said stent or stent graft is knitted from multiple wires of different diameter.

8. The tubular knitted stent or stent graft according to claim 1, wherein radiopaque wire cores are used for knitting the said stent or stent graft or wherein radiopaque elements are attached to the said stent or stent graft in order to increase fluoroscopic visibility.

9. The tubular knitted stent or stent graft according to claim 1, the stent or stent graft having an elongated tubular structure, wherein the stent or stent graft comprises dome or conical shaped sections along its elongated tubular structure.

10. The tubular knitted stent or stent graft according to claim 1, comprising nitinol.

11. A method for fabricating a tubular stent or stent graft for placement in a lumen or body passage, the method comprising:
    knitting a tubular stent or stent graft which is compressible and has a compressed and a non-compressed outer diameter, the stent or stent graft having knitted loops each having a loop width, wherein the loop width to non-compressed outer diameter ratio is larger than 0.2 for at least one knitted loop;

crimping the stent or stent graft to a compressed outer diameter smaller than the non-compressed outer diameter.

12. The method according to claim 11, wherein knitting the tubular stent or stent graft comprises using a knitting head having needle slots designed to support and guide knitting needles, wherein a plurality of knitting needles are used in at least one needle slot.

13. The method according to claim 11, wherein knitting the tubular stent or stent graft comprises using a knitting head having needle slots designed to support and guide knitting needles, the needle slots being separated by a verge between them, wherein at least one pair of adjacent needle slots have a top of a verge between them removed, so that any two adjacent loops formed by at least one needle guided by the at least one pair of needle slots coincide.

* * * * *